United States Patent [19]  [11] 4,229,535
Ishihara et al.  [45] Oct. 21, 1980

[54] METHOD FOR PREPARING MULTHIOMYCIN

[75] Inventors: Eisuke Ishihara, Miyanonishi; Hiroshi Yonehara, Tokyo; Katsuyuki Akasaki, Shimizu; Masao Minowa; Katsumi Kobayashi, both of Shizuoka, all of Japan

[73] Assignee: Kumiai Chemical Industry Co., Ltd., Tokyo, Japan

[21] Appl. No.: 892,917

[22] Filed: Apr. 3, 1978

Related U.S. Application Data

[63] Continuation of Ser. No. 681,198, Apr. 28, 1976, abandoned.

[30] Foreign Application Priority Data

Oct. 28, 1975 [JP] Japan ................................ 50-128910

[51] Int. Cl.$^3$ ............................................. C12P 13/00
[52] U.S. Cl. ..................................... 435/128; 435/130; 435/169; 435/244
[58] Field of Search ............... 435/128, 129, 130, 244, 435/169, 170

[56] References Cited

PUBLICATIONS

Teruo Tanaka, et al. The Journal of Antibiotics, vol. 23, No. 5, pp. 231–237, 1970.
The Difco Manual, 9th Ed., pp. 264–265, 1953.

*Primary Examiner*—Robert J. Warden
*Attorney, Agent, or Firm*—Stevens, Davis, Miller & Mosher

[57] ABSTRACT

The present invention relates to a method of cultivation and extraction of multhiomycin, an antibiotic, and relates also to a veterinary medicine containing multhiomycin as an effective ingredient and more particularly, the present invention provides a method for obtaining multhiomycin by cultivating a multhiomycin-producing fungus such as Streptomyces sp. 8446-CC1 belonging to genus Streptomyces in a culture medium containing a sulfur-containing amino acid and treating the culture medium with a mixed solvent of alcohols and halogenated hydrocarbons or ketones and provides a medicine for promoting growth of animals and preventing various kinds of diseases of animals which contains multhiomycin as an essential component.

5 Claims, 2 Drawing Figures

METHOD FOR PREPARING MULTHIOMYCIN

This is a Continuation of application Ser. No. 681,198 filed Apr. 28, 1976, now abandoned.

BACKGROUND OF THE INVENTION

1. Field of the Invention

The present invention relates to a method of cultivation and extraction of multhiomycin, an antibiotic, and relates also to a veterinary medicine containing multhiomycin as an effective ingredient. More particularly, this invention provides a method for obtaining multhiomycin by cultivating a multhiomycin-producing fungus such as Streptomyces SP 8446-CC1 belonging to genus Streptomyces in a culture medium containing a sulfur-containing carboxylic acid and treating the culture medium with a mixed solvent of alcohols and halogenated hydrocarbons or ketones, and provides a medicine for promoting growth of animals and preventing various kinds of diseases of animals which contain multiomycin as an essential component.

2. Description of the Prior Art

The present inventors have pursued extensive studies on various kinds of antibiotics produced by microorganisms and continued further study on multhiomycin, an antibiotic disclosed in the Journal of antibiotics Vol. XXIII, No. 5, pp 231-237 (1970) by H. Yonehara (one of the present inventors) et al.

H. Yonehara et. al. reported in the said publication that multiomycin is a new antibiotic obtained from the micelium of *Streptomyces antibioticus* sp 8446-CC, which is extracted with methanol and purified by silica gel chromatography and forms yellow needle-shaped crystals, melts at above 300° C. and has no or negligible optical activity. $C_{44}H_{45}O_{11}N_{11}S_5$ was suggested for its molecular formula by elemental analysis and molecular weight determination and and it was further found to exhibit inhibitory activity against gram-positive bacteria but no activity against gram-negative bacteria, mycobacteria and fungi. However, the above authors did not find that multhiomycin is useful as veterinary medicine.

SUMMARY OF THE INVENTION

The inventors continued an extensive study on Multhio mycin and the use thereof and through their continued studies accomplished the present invention.

The object of the present invention is to provide a method of cultivation of multhiomycin.

Another object of the present invention is to provide a method of extraction of multhiomycin from the cultivating broth in a high pure state and in a good yield.

A further object of the present invention is to provide a veterinary medicine containing multhiomycin as an essential component.

A still further object of the present invention is to provide a method of purification of multhiomycin.

DESCRIPTION OF THE PREFERRED EMBODIMENTS

Figure 1:
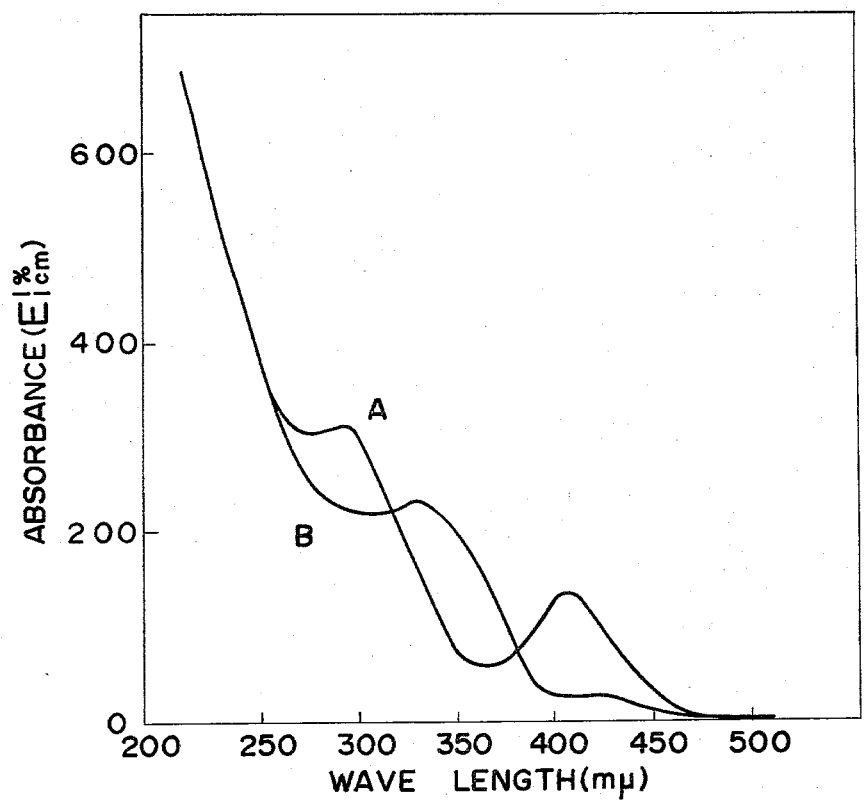
FIG. 1 is a graph showing the ultraviolet absorption curves of multhiomycin in alkaline methanol (A) and in neutral or acid methanol (B)

Streptomyces sp. 8446-CC1 used in the present invention has the following morphological cultural and physiological characteristics.

Cultural characteristics of Streptomyces sp. 8446-CCl in various culture medium

| Medium | Cultural characteristics |
|---|---|
| Sucrose nitrate agar | G: thin, colorless to yellowish gray |
| | AM: abundant, powdery, white |
| | SP: very slight, yellowish gray |
| Glycerol-nitrate agar | G: thin, colorless to yellowish gray |
| | AM: poor, powdery, white |
| | SP: very slight, yellowish gray |
| Glucose-asparagine agar | G: moderate, yellowish gray with pale yellowish brown reverse |
| | AM: abundant, velvety, light gray to light brownish gray |
| | SP: slight, pale yellowish brown |
| Glycerol-calcium malate agar | G: moderate, spreading and penetrating into agar, yellowish gray |
| | AM: abundant, velvety, light brownish gray with whitish patch |
| | SP: very slight, yellowish gray |
| Starch agar | G: moderate, spreading and penetrating into agar, yellowish gray with light brownish gray reverse |
| | AM: abundant, velvety, light gray with brownish tinge |
| | SP: very slight, yellowish gray |
| Peptone-beef extract agar | G: moderate, pale yellowish brown with yellowish brown reverse |
| | AM: poor, powdery, white at margin of colony |
| | SP: yellowish brown |
| Glucose-peptone-beef extract agar | G: thick and wrinkled, yellowish gray |
| | AM: poor, powdery, white at margin of colony |
| | SP: yellowish brown |
| Glucose-peptone-agar | G: thin, pale yellow |
| | AM: none |
| | SP: slight, pale, yellow |
| Glucose-cesein digest-yeast-beef agar | G: moderate and wrinkled, pale yellowish brown reverse |
| | AM: moderate, velvety, light gray with brownish tinge |
| | SP: slight, pale yellowish brown |
| Oatmeal-yeast extract agar | G: moderate, spreading and penetrating into agar yellowish gray |
| | AM: abundant, velvety, light gray with brownish tinge |
| | SP: very slight, yellowish |
| Potato plag | G: thick and wrinkled |
| | AM: abundant, light gray with brownish tinge |
| | SP: dark brown |
| LOEFFLER'S blood serum | G: moderate, dark brown |
| | AM: poor, powdery, white |
| | SP: dark brown |
| Gelation | G: surface ring, pale yellowish brown |
| | AM: none |
| | SP: brown |
| Milk | G: surface ring, pale yellowish brown |
| | AM: abundant, powdery white |
| | SP: brown to dark brown |
| Cellulose medium | G: thin, colorless |
| | AG: abundant, powdery, light gray |
| | SP: none |
| Glycerin-asparagin agar | G: moderate, yellowish gray to pale yellow |
| | AM: abundant, powdery, bronwhite to light brown gray |
| | SP: very slight, yellowish gray |
| Thyrosine agar | G: moderate grayish yellow brown |
| | AM: moderate, powdery, white |
| | SP: dark yellow brown |
| | G: thick, pale yellow brown to grayish yellowish brown |

-continued

| Cultural characteristics of Streptomyces sp. 8446-CC1 in various culture medium | |
|---|---|
| Medium | Cultural characteristics |
| Yeast-malt agar | AM: abundant, velvety, light brownish gray<br>SP: pale yellow brown<br>G: thin, yellowish gray |
| Oatmeal agar | AM: abundant, velvety, light brownish gray<br>SP: slight, yellowish gray |

G: Groth, AM: Aerial mycelium, SP: Soluble pigments

In the table above, color was determined by the method described in "Color Harmony Manual" published by Container Comporation of America.

Physiological Properties

Optimum growth condition: pH 7.0—aerobio
Growth condition: pH, 6.2–7.8, ungrowable under 5° C. and above 45° C. and ungrowable under anaerobic condition (ungrowable in a lower layer in the case of stab culture in a tale yeat-malt agar culture medium)
Color production: prepare deep brown color in a natural culture medium and melanine color in tyrosine culture medium
Hydrogenation of starch: liquify
Decomposition of cellulose: no decomposition
Reduction of nitrate: reduct
Decomposing power of protein: gelation liquification milk peptonization, blood serum liquefaction
Utilization of hydrocarbons: utilizes as carbon source glucose, rhamnose, mannose, milk sugar, raffinose, mannitol, sucrose, glycerin and salicin, and does not utilize arabinose, fructose and cellulose.

Cultural and physiological characteristics of the strain 8446-CC$_1$ are as shown in the above. The strain was determined to belong to "Gray series" of TRESER and BACKUS by the fact that the color of aerial mycelium was light gray to light brownish gray. The substrate mycelium or reverse side of colony showed no distinctive colors (yellowish gray to yellowish brown) on all media. Soluble pigments were produced slightly and not distinctively (yellowish gray to pale yellowish brown) on synthetic or some organic media. Chromogenic pigments (yellowish brown to dark brown) were produced on most organic media and melanoid pigment on tyrosine agar. Judging from the above-described morphological cultural physiological characteristics, Streptomyces sp. 8446-CC1 is considered to be a strain belonging to *Streptomyces antibioticus*. This strain was deposited with the Fermentation Research Institute Agency of Industrial Science and Technology under Deposit No. FERM-P No. 3284 and the samples of the strain can be issued to the third parties after the Japanese Patent Application No. 128910/1975 which is the base application of this application, is open.

Above mentioned Streptomyces sp.-8446-CC1 strain belonging to genus Streptomyces is not the only strain usable for production of multhiomycin of this invention, but it is also possible to use any kind of strain which belongs to genus Streptomyces and is capable of producing multhiomycin.

For obtaining multhiomycin, a multhiomycin-producing strain belonging to genus Streptomyces is cultured in a culture medium which comprises a carbon source such as glucose, maltose, fructose, sucrose, lactose, molasses, starch, dextrine or the like, a nitrogen source such as soybean flour, peanut flour, cottonseed flour, meat extract, corn steep liquour, yeast, glutamic acid, urea, sodium nitrate, ammonium nitrate, ammonium phosphate or the like and as an essential nutrient 0.0005 to 10% by weight, preferably 0.01 to 5% by weight, of sulfor-containing carboxylic acid or its derivatives such as thioglycollic acid, thioglycollic acid amide, thiomalic acid, thiobenzoic acid, methionine, cysteine, cystine or ammonium salt, alkali metal salt or alkali earth metal salt thereof. Addition of the said sulfur-containing carboxylic acid to the culture medium enhances the production of multhiomycin by 2 to 4 times that attained when no such acid is added. If necessary, it is also possible to add to the culture medium sodium chloride, phosphate or a very small amount of metal ions. A culture medium which contain dextrine, dry yeast, methionine, sodium chloride and calcium carbonate, and which contain starch, cottonseed flour, methionine, sodium chloride and calcium carbonate are best suited for production of multhiomycin.

Although cultivation of the multhiomycin-producing strain can be accomplished by solid culture, it is more advantageous to employ liquid culture, particularly submerged culture, for mass cultivation. Cultivation can be conducted under an aerobic or semi-aerobic condition. For instance, it is possible to carry out cultivation under flow of germ-free air or by surface culture with no aeration. Cultivation temperature is usually within the range of 10° to 50° C., preferably 23° to 32° C., but in most cases a temperature of around 27° C. is found to be optimal.

Generally, production of multhiomycin reaches its maximum after about 1 to 9 days cultivation in the case of shaking culture and in about 1 to 8 days cultivation in the case of aerated tank culture. In performing cultivation, a mineral acid such as hydrochloric acid or sulfuric acid or an organic acid such as acetic acid or oxalic acid is added in an appropriate amount to maintain the pH of the culture solution at 4.0 to 9.0, preferably at 5.5 to 8.5, to maximize the production of multhiomycin.

Since multhiomycin is present in both the culture broth and the mycelium containing solids, collection of multhiomycin from the cultured product after cultivation, can be conducted by collecting multhiomycin separately from the filtrate and the solid mass after filtering out the solids and then combining together the collected mass or immediately collecting multhiomycin from the culture solution containing the solids. The collection of multhiomycin can be accomplished by any suitable known methods generally used in separating and collecting the antibiotics from a culture of microorganisms or by combining such methods.

For collecting multhiomycin from the culture broth from which the mycelium-containing solids have been filtered out, it has been generally attempted to extract the object substance a solvent immiscible in water, such as for example esters, butanol, amylalcohol, benzene, methyl isobutylkentone or the like, but further study on extraction solvents conducted by the present inventors has revealed that multhiomycin present in the filtrate can be extracted at a higher efficiency by a mixed solvent prepared by mixing an alcoholic solvent such as methanol, ethanol, is isopropanol, n-propanol, butanol, cellosolves or the like with halogenated hydrocarbon solvent such as methyl chloride, dichloroethane, chloroform, carbon tetrachloride, chlorobromomethane, dichloromethane, chlorobromoethane, trichloroethane, dichloropropane, chlorobutane or the like at an mixing ratio of 1:0.1 to 10, preferably 1:1 to 7.

For instance, when a culture broth obtained from cultivation is divided into two portions and one portion is subjected to three successive extractions by butyl acetate and the other is extracted a mixed solvent of methanol and chloroform mixed in the ratio of 1:4, it is found that the extracted amount of multhiomycin in the case of the mixed solvent is four times as high as that in the case of butyl acetate alone. Also, the extraction of multhiomycin from the mycelium-containing solids has been generally accomplished by a single solvent such as acetone, methanol, ethanol or the like, but as a result of our study on the solvents for extracting multhiomycin from solids, it was found that the best extraction can be obtained in the case of extraction using a solvent consisting of a ketone such as acetone, methyl ethyl ketone or the like and an alcoholic solvent such as methanol, thanol, butanol, phenol or the like in the ratio of 1:0.1 to 20, or using a mixture solvent consisting of a halogenated hydrocarbon solvent and an alcoholic solvent used in extraction of multhiomycin from the filtrate. For instance, the collection rate using methanol attained in case of extracting multhiomycin from the fungus containing solids obtained under the same conditions by three successive extraction operations is 2.62 gr. as measured in conversion to the purity basis, whereas the collection rate attained from initial extraction with methanol and additional extraction with a mixed solvent of methanol and methylene chloride (mixed in the ratio of 1:4) is as high as 4.46 gr.

Now the methods of cultivation as well as the methods for collecting multhiomycin according to the present invention are described in detail by way of embodiments thereof.

EXAMPLE 1

Cultivation of multhiomycin (addition of sulfur-containing carboxylic acid)

Methionine, cystein and thioglycolic acid were added at the proportions shown in Table 1 to a culture base having the following composition:

Dextrine: 2.5%
Dry yeast: 2.0%
Sodium chloride: 0.5%
Calcium carbonate: 0.4% and Streptomyces sp. 8446-CC1 strain was inoculated in each of the thus prepared culture media and subjected to cultivation at 28° C., and the multhiomycin potency on the 4th day after start of the cultivation was measured. The results obtained are shown in Table 1. Multhiomycin was extracted by a mixed solution of acetone and methanol (in the ratio of 4:1) from the culture mycelium separated centrifugally, and diluted with a 30% acetone-containing 0.1 M phosphoric acid buffer solution (pH 8).

And the potency of the solution was determined according to the cylinder agar plate method by using *Bacillus subtilis* as test organism.

TABLE 1

| Amount of additives added to basic culture medium % (w/w) | | | Strength on 4th |
|---|---|---|---|
| Methionine | Cystin | thioglycolic acid | day (γ/ml) |
| 0.001 | | | 353 |
| 0.005 | | | 401 |
| 0.01 | | | 517 |
| 0.05 | | | 728 |

TABLE 1-continued

| Amount of additives added to basic culture medium % (w/w) | | | Strength on 4th |
|---|---|---|---|
| Methionine | Cystin | thioglycolic acid | day (γ/ml) |
| 0.1 | | | 1,012 |
| 0.5 | | | 869 |
| 1.0 | | | 470 |
| 3.0 | | | 329 |
| | 0.001 | | 305 |
| | 0.01 | | 634 |
| | 0.1 | | 842 |
| | 1.0 | | 540 |
| | 3.0 | | 423 |
| | | 0.001 | 282 |
| | | 0.01 | 336 |
| | | 0.1 | 578 |
| | | 1.0 | 719 |
| | | 3.0 | 318 |
| basic culture medium (no addition) | | | 235 |

EXAMPLE 2

Cultivation of multhiomycin (control of pH)

Streptomyces sp. 8446-CC1 strain was inoculated in a culture medium of the following composition:

Starch: 2.5%
Cottonseed flour: 2.0%
Sodium chloride: 0.5%
Calcium carbonate: 0.4% and pH of the culture solution was controlled between 6.5 and 8.5 by automatic injection of 2 N hydrochloric acid by an automatic acid injector. For sake of comparison, there was also prepared a control group in which the pH of the culture medium was initially adjusted at 5.6.

Cultivation was carried out at 28° C., and the multhiomycin potency of the extracted solution was determined. The results obtained are shown in Table 2 below.

TABLE 2

| | 3rd day | | 5th day | |
|---|---|---|---|---|
| Test groups | Potency γ/ml | pH | Potency γ/ml | pH |
| Group having controlled pH of 8.5 | 173 | 6.5 | 769 | 8.5 |
| Nontreated (pH 5.6–9.2) | 157 | 5.9 | 248 | 9.2 |

EXAMPLE 3

Collection test of multhiomycin by using mixed solvent

A seed culture solution of Stremptomyces sp. 8446-CC1 strain was inoculated in 100 l of culture medium (with adjusted pH of 5.6) containing 2.5% of starch, 2% of cottonseed flour, 0.1% of methionine, 0.5% of socium chloride and 0.4% of calcium carbonate. The culture medium was subjected to culturing at 27° C. under agitation of 300 r.p.m. and aeration of 15 l/min. As production of multhiomycin reached its maximum after 80 hours cultivation, cultivation was stopped at that point and the mycelium were filtered out to obtain about 48 kg of wet mycelium. These mycelium were then well mixed up and divided into 27 groups of 1 kg per group, and each group was extracted by 1.5 l of methanol and filtrated. The second extraction from each specimen was carried out using 1.5 l of each sample of mixed solvents shown in Table 3, then each methanol extracted solution and each said mixed solvent were combined together and subjected to vacuum distillation (at 60° C.) to fractionate each solvent from the extracted solution, and then 50 cc of each remaining aqueous solution was further extracted with 100 cc of ethyl acetate. Then ethyl acetate was distilled off under vacuum from each said ethyl acetate extracted solution and each remaining oily substance was dissolved in one of the specimens of mixed solvents shown in Table 3, and n-hexan in an amount 1.5 times as much as that of each dissolved solution was added portionwise to the solution, whereby yellow sediment of multhiomycin was obtained. Each such sediment was collected on a glass filter and once washed with 10 ml of methanol to collect crude crystals of multhiomycin. Then the purity of each clude crystal specimen was measured by the cup method above mentioned, and the purity-converted total weight (gross activity) was determined from the value obtained and each crystal weight.

TABLE 3

| Mixed solvents for 2nd extraction | | | | Crude crystal Weight (mg) | Purity (%) | Converted into purity Total weight (mg) |
|---|---|---|---|---|---|---|
| Chloroform | 10: | methanol | 1 | 2242 | 68.6 | 1538 |
| " | 5: | " | 1 | 2574 | 77.3 | 1990 |
| " | 4: | " | 1 | 2231 | 91.5 | 2041 |
| " | 2: | " | 1 | 2299 | 82.4 | 1895 |
| " | 1: | " | 1 | 2738 | 73.3 | 2007 |
| 1,2-dichloroethane | 10: | " | 1 | 2324 | 70.5 | 1638 |
| 1,2-dichloroethane | 5: | " | 1 | 2540 | 82.0 | 2083 |
| 1,2-dichloroethane | 4: | " | 1 | 2563 | 80.2 | 2056 |
| 1,2-dichloroethane | 2: | " | 1 | 2271 | 63.5 | 1442 |
| 1,2-dichloroethane | 1: | " | 1 | 1919 | 71.3 | 1368 |
| trichloroethylene | 10: | " | 1 | 1913 | 69.8 | 1335 |
| trichloroethylene | 5: | " | 1 | 2414 | 74.0 | 1786 |
| trichloroethylene | 4: | " | 1 | 2515 | 68.2 | 1715 |
| trichloroethylene | 2: | " | 1 | 1822 | 82.5 | 1503 |
| trichloroethylene | 1: | " | 1 | 2000 | 78.7 | 1574 |
| aceton | 10: | " | 1 | 2072 | 73.5 | 1523 |
| " | 5: | " | 1 | 2593 | 72.3 | 1875 |
| " | 4: | " | 1 | 2855 | 70.5 | 2013 |
| " | 2: | " | 1 | 2263 | 93.0 | 2105 |
| " | 1: | " | 1 | 2134 | 88.3 | 1884 |
| chloroform | 10: | phenol | 1 | 2345 | 63.2 | 1482 |
| " | 5: | " | 1 | 2420 | 83.6 | 2006 |
| " | 4: | " | 1 | 2755 | 94.5 | 2603 |
| " | 2: | " | 1 | 2642 | 82.3 | 2174 |
| " | 1: | " | 1 | 2015 | 72.7 | 1465 |
| aceton | 10: | phenol | 1 | 2445 | 50.7 | 1240 |
| " | 5: | " | 1 | 2721 | 84.2 | 2291 |
| " | 4: | " | 1 | 2863 | 91.3 | 2614 |
| " | 2: | " | 1 | 2821 | 86.4 | 2437 |
| " | 1: | " | 1 | 2562 | 75.6 | 1937 |
| chloroform | 4: | ethanol | 1 | 2239 | 76.3 | 1708 |
| 1,2-dichloroethane | 4: | " | 1 | 2197 | 73.7 | 1619 |
| trichloroethylene | 4: | " | 1 | 2440 | 69.8 | 1703 |
| acetone | 4: | " | 1 | 2716 | 81.3 | 2208 |
| methanol | single | solvent | | 2067 | 55.3 | 1143 |
| ethanol | | " | | 2183 | 41.5 | 906 |

EXAMPLE 4

Collection test of multhiomycin by using mixed solvent

A need specific culture solution of Streptomyces sp 8446-CC1 strain was inoculated in 60 l of a culture medium (with adjusted pH of 5.6) containing 2.5% of dextrine, 2.0% of dry yeast, 0.5% of sodium chloride and 0.4% of calcium carbonate. The culture medium was subjected to aerated cultivation under agitation and aeration of 15 l/min. When multhiomycin production reached its maximum level after 96 hours, the cultivation was stopped and the cultured solution was equally divided into two portions.

(1) In case of using methanol-chloroform mixed extraction solvent

Mycelium were filtered out from one of the two portions of the culture to obtain about 9.5 kg of set mycelium. These mycelium were extracted first with 15 l of methanol and then with 15 l of mixed solvent of methanol and chloroform (mixed in the ratio os 1:4 by volume), and then the extractant was mixed with the methanol extraction solution and subjected to vacuum concentration at 60° C. to obtain 500 ml of water-containing residue. This was again extracted with 1 l of ethyl acetate and the latter was subjected to vacuum concentration to obtain an oily substance, which was then dissolved in a mixed solvent of methanol and chloroform (mixed in the ratio of 1:4 by volume), and to this solution was further added portionwise normal hexan in an amount 1.5 times that of each dissolved solution, whereby yellow multhiomycin precipitated. The precipitate was filtered out, washed with 10 ml of methanol and dried, obtaining 4.8 gr of crude crystals of multhiomycin (with purity of 93%).

(2) In case of using methanol (prior art)

Mycelium were filtered out from another portion of the culture to obtain about 9.8 kg of wet mycelium, and these mycelium were extracted three times with 15 l of methanol and the extraction solution was concentrated under vacuum to obtain 750 ml of water-containing residue. This residue was further extracted with 1 l of ethyl acetate and the ethyl acetate extracted solution was vacuum-concentrated into 120 ml of concentrated mass, to which was added n-hexane portionwise to precipitate yellow multhiomycin. This precipitate was filtered out and washed with 10 ml of methanol to obtain 4.6 gr of crude crystals of multhiomycin (with purity of 57%).

The crude multhiomycin obtained in the processes (1) and (2) above mentioned can be refined by recrystallization with a mixture of dimethyl formamide and ethyle acetate, or by column chromatography of silica gel using a mixture of dimethyl formamide and ethyl acetate as a developing solvent. The refined product is in the form of needle crystal.

EXAMPLE 5

A seed culture solution of Streptomyces sp 8446-CC1 strain was inoculated in 30 l of a culture medium (with adjusted pH of 5.6) containing 2.5% of dextrine, 2.0% of dry yeast, 0.5% of sodium chloride and 0.4% of calcium carbonate. The culture medium was subjected to culturing under agitation by agitator and under aeration with 15 l/min. of air.

As the production of multhiomycin reached its maximum level after 96 hours cultivation, the cultivation was suspended at that point and the myceline were filtered out to obtain about 10 kg of wet mycelium. These mycelium were extracted first with 15 l of methanol and then with 15 l of a mixed solvent of acetone and methanol mixed in the mixing ratio of 4:1 in volume and then the two extracted solutions were combined and subjected to vacuum distillation (at 60° C.) to separate methanol and acetone from the mixed solution, and 500 ml of remaining aqueous solution was further extracted with 1 l of mixed solvent of isopropanol and dichloroethane mixed in the ratio of 1:4 in volume, isopropanol and dichloroethane were distilled off under vacuum (at 60° C.) from this isopropanol-dichloroethane mixed extracted solution and the residual oily substance was dissolved in a mixed solvent of isopropanol and dichloroethane (mixed in the ratio of 1:4 in volume), and to this solution was added portionwise, n-hexan in amount 1.5 times as much as that of the solution, whereby yellow sediment of multhiomycin was obtained. This sediment was collected on a glass filter and washed once with 10 ml of methanol, obtaining 6.2 gr of crude crystals of multhiomycin (with a purity of 90%).

1 gr of these crude crystals of multhiomycin was dissolved in 800 ml of ethyl acetate containing 10% of DMF and then allowed to stand at room temperature (about 20° C.) for two days, consequently obtaining 660 mg of needle crystals of multhiomycin (with a purity of 100%).

The antibiotic multhiomycin obtained according to this invention has the following physicochemical properties.

The elemental analysis of multhiomycin showed the following constituents: C 49.74; H 4.17; O 16.74; N 15.13; and S 15.03, and the molecular weight measured by the vapor pressure method was 1064. It is anticipated from these facts that multhiomycin has the molecular formula, $C_{44}H_{45}O_{11}N_{11}S_5$. Melting point (decomposition point) of this antibiotic is higher than 300° C.

Figure 2:
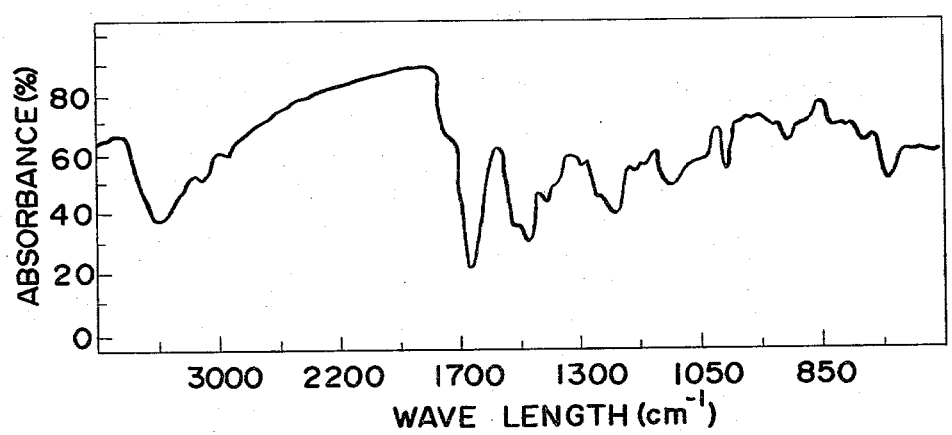
FIG. 2 shows an infrared absorption curve of the multhiomycin as measured in the form of a potassium bromide tablet.

The ultraviolet absorption curve of multhiomycin is as shown in the graph of FIG. 1. As seen from the graph, it shows the maximum absorptivity at 328 m$\mu$ ($E_{1\ cm}^{1\%} 220$) and 420 m$\mu$ ($E_{1\ cm}^{1\%} 20$) in the neutral or acid methanol (B), while in the alkaline methanol (A) it shows the maximum absorptivity at 292 m$\mu$ ($E_{1\ cm}^{1\%} 255$) and 406 m$\mu$ ($E_{1\ cm}^{1\%} 132$). FIG. 2 shows the infrared absorption curve of multhiomycin (in potassium bromide tablet), from which it will be seen that high absorptivity is observed at 3380 cm$^{-1}$, 1660 cm$^{-1}$, 1520 cm$^{-1}$, 1470 cm$^{-1}$, 1200 cm$^{-1}$, 1110 cm$^{-1}$, 1015 cm$^{-1}$, 910 cm$^{-1}$ and 750 cm$^{-1}$.

Multhiomycin is soluble in dimethylformamide, dimethyl sulfoxide and pyridine, but is only slightly soluble in ethyl acetate, methanol, ethanol and dioxane and is insoluble in water, acetic acid, n-hexane, ether, chloroform and many other organic solvents.

As for color reaction of multhiomycin, it develops various colors by the ferric chloride reagent, Folin's reagent and Lemieux reagent, but it develops no color by the ninhydrin reagent, Fehling's reagent and Ponceau-3R reagent or in the buret reactions.

Multhiomycin remains stable when heated in an aqueous solution at 100° C. at a pH of 2 to 5 for five minutes. It is a slightly acidic and is in the form of yellow needle crystal. No optical activity is observed in its 1% solution.

As a medicine for animals using Multhiomycin, the fungus containing multhiomycin obtained by the cultivation of Spreptomyces sp. 8446-CC1, or multiomycin producing fungus, crude multhiomycin or refined multhiomycin can be directly administrated to the animals in the form of a solution, emulsion, suspension, wettable powder, dust, tablets or injection, or administrated to the animals by adding to their feed or drinking water. Multhiomycin can also be used as a growth stimulator for a wide variety of animals including poultry such as laying hens, broilers, turkeys, ducks, etc., livestock such as cattle, horses, pigs, sheeps, goats, mink, etc., pet animals such as dogs, cats, pigeons, etc., or laboratory animals such as mice, rats, rabbits, etc.

In administering multhiomycin to said animals, it may be directly blended in feed or drinking water. More effectively, multhiomycin is once formed into a solution or emulsion or into a wettable powder or suspension and then added to feed or drinking water given to the animals. In case of using multhiomycin in the form of solids such as wettable powder or suspension, good results can be obtained if the particle size of multhiomycin is within the range of 1 to 100$\mu$, preferably less than 5$\mu$. This is due to the property of multhiomycin of not being absorbed in the body of the animal to which it is administered.

As for the optimal dosage of multhiomycin for animals, it is usually given in an amount of 0.1 to 500 ppm, preferably 0.5 to 100 ppm, by blending it in feed or drinking water, although the amount is somewhat varied depending upon the degree of growth of the object animal. This level of concentration is far lower than the dosage required for various kinds of diseases of animals.

In case of using multhiomycin in mixture (blend) with feedstuff, multhiomycin or its mixture with an extender or diluent such as starch, dextrose, dextrine, calcium carbonate, kaolin or the like is crushed by a crushing machine such as jet pulverizer to prepare a dust, wettable powder or suspension, then this is diluted with a suitable amount of water and absorbed or spread in a feedstuff such as soybean meal to make a feed containing about 0.5 to 10% of multhiomycin, and then this is further blended with feedstuff so that multhiomycin has the prescribed concentration therein. In case that multhiomycin is in the form of a solution or emulsion, it is adsorbed or spread in a feedstuff directly or after diluting it with water to prepare a feed containing about 0.5 to 10% of multhiomycin, and then this is blended with feedstuff in such as amount as to provide a predeterminded concentration.

Multhiomycin can be added to any type of feedstuff generally used for animals, such as corn, milo, soybean meal, soybean flour, lucern meal, fish meal, rice bran, wheat flour, wheat bran, fats, cottonseed meal, etc.. It is also possible to blend other additives therewith, for example a surfactant or adjuvants such as sodium asparaginate, sorbitan monostearate, sorbitan monolaurate, Tween, calcium carbonate, sodium chloride, choline chloride, vitamines, calcium pantothenate, nicotinic acid mode, folic acid, iron surfate, magnesium sulfate, zinc sulfate, cobalt sulfate, amino acids, etc., or other feed additives such as sulfa drugs, various kinds of coccidiostats, and other antibiotics and antiparasitics.

Multhiomycin is efficacious not only for promoting growth of animals but also for improving feed efficiency, egg-laying and fertilization rates as well as for preventing watery faces of fowls.

Now the physiological effects of multhiomycin are described in detail in the results of tests on promotion of growth of animals and other matters.

EXAMPLE 6

500 chickens Hubbard (250 males and 250 females) one-day old after hatching were divided into five groups each of which consisted of 100 chickens (with the same number of males and females) and these groups of chicks were fed the feeds containing multhiomycin of 0.5, 1, 2 and 4 ppm, respectively, with the control group being fed with feeds to which no multhiomycine was added and such feeding was continued for eight weeks according to a floor pen system.

The results of the test are shown in Table 4 below, from which it is noted that the average body weight of the 8-week old chickens in the multhiomycin-added feed groups is higher by 6.4 to 9.0% than that of the counterparts in the control group, while the feed efficiency is improved by an amount of 0.13 to 0.24 over the control.

TABLE 4

Change of average body weight and feed efficiency

| Group | 0-week old | 2-week old | 4-week old | 6-week old | 8-week old | Feed efficiency |
|---|---|---|---|---|---|---|
| control | 43 | 245 | 685 | 1330 | 1825 | 2.44 |
| 0.5 ppm | 43 | 245 | 706 | 1412 | 1942 | 2.31 |
| 1.0 ppm | 43 | 247 | 719 | 1419 | 1951 | 2.30 |
| 2.0 ppm | 43 | 250 | 723 | 1423 | 1962 | 2.25 |
| 4.0 ppm | 43 | 247 | 726 | 1431 | 1989 | 2.20 |

(NOTES)
(1) Each numerical value in the table is a mean value (gr).
(2) Feed efficiency = total amount of feed ingested during the entire test period ÷ body weight gain during the entire test period.

Composition of basal feed (1) Starter feeds (used in 0 to 4-week period)

| | |
|---|---|
| Corn | 49.5% |
| Soybean meal | 24.5 |
| Milo | 12.2 |
| Lucerne meal | 4.0 |
| Fish meal | 6.5% |
| Sodium chloride | 0.3 |
| Calcium carbonate | 1.5 |
| Calcium phosphate | 1.0 |
| Premix (*) | 0.5 |

125 ppm of Amprolium (Trade mark) was added as a coccidiosis preventive.

(2) Finisher feeds (used in 5 to 8 week period)

| | |
|---|---|
| Corn | 52.0% |
| Soybean meal | 10.0 |
| Milo | 14.5 |
| Fish meal | 9.8 |
| Fats | 7.0 |
| Lucerne meal | 3.5 |
| Sodium chloride | 0.2 |
| Calcium carbonate | 1.5 |
| Calcium phosphate | 1.0 |
| Premix (*) | 0.5 |

125 ppm of Amprolium (Trade mark) was added as a coccidiosis preventive.

(*) Premix contains vitamin A, vitamin D$_3$, vitamin E, vitamin B$_1$, vitamin B$_2$, vitamin B$_6$, vitamin B$_{12}$, pantothenis acid, nicotinic acid, choline chloride, folic acid, iron sulfate, copper sulfate, cobalt and zinc.
Note:
mixture of 1-(4-amino-2-propyl-5-pyrimidinyl methyl)-2-picolium hydrochloride and methyl-4-acetamido-2-ethoxybenzoate (1000:64)

EXAMPLE 7

400 broiler chickens (200 males and 200 females were equally divided into 4 groups (each group consisting of 100 chickens) and 2 ppm of multhiomycin with prescribed particle sizes was added to the feeds to be given to the respective groups except for the control group, to which ordinary commercial feed (produced by Zenno) were given and the feeding test was conducted by using such feeds for eight weeks according to a floor pen system.

Multhiomycin-blended feeds were prepared in the following way. That is, a wettable powder consisting of 20% of multhiomycin with various particle sizes, 40% of calcium carbonate, 30% of dextrose, 15% of kaolin and 5% of sorbitan monostearate was diluted in water and then spread in soybean meal to make a feed material containing 2% of multhiomycin, and then this was further blended with feedstuff so that multhiomycin was contained in an amount of 2 ppm therein.

It was found as a result that the smaller is the particle size of multhiomhcin added, the higher is the degree of improvement.

TABLE 5

Change of average body weight and feed efficiency

| Group | Particle size of multhio-mycin(μ) | 0-week | 2-week | 4-week | 6-week | 8-week | Feed efficiency |
|---|---|---|---|---|---|---|---|
| Control | — | 42 | 236 | 689 | 1323 | 1812 | 2.44 |
| Added with multhio-mycin | 52–44 | 42 | 227 | 695 | 1380 | 1891 | 2.34 |
| Added with multhio-mycin | 43–37 | 42 | 242 | 705 | 1389 | 1902 | 2.32 |
| Added with multhio-mycin | 3–5 | 42 | 252 | 733 | 1438 | 1975 | 2.21 |

(Notes)
(1) Each numerical figure in the table is a mean value (gr).
(2) Feed efficiency = total amount of feed ingested during the entire test period ÷ body weight gain during the entire test period.

| Feed materials | Used in 0 to 4-week period | Used in 5 to 8-week period |
|---|---|---|
| Corn | 49.5% | 52.0 |
| Soybean meal | 24.5 | 10.0 |
| Milo | 12.2 | 14.5 |
| Fats | — | 7.0 |
| Lucerne meal | 4.0 | 3.5 |
| Fish meal | 6.5 | 9.8 |
| Sodium chloride | 0.3 | 0.2 |
| Calcium carbonate | 1.5 | 1.5 |
| Calcium phosphate | 1.0 | 1.0 |
| Premix (*) | 0.5 | 0.5 |
| Coccidium preventive (Amprolium) | 125 ppm | |

(*) Premix contains vitamin A, vitamin D$_3$, vitamin E, vitamin B$_1$, vitamin B$_2$, vitamin B$_6$, vitamin B$_{12}$, pantothenic acid, nicotinic acid, choline chloride, folic acid, iron sulfate, copper sulfate, cobalt and zinc.

EXAMPLE 8

600(180-day-old)egg-laying hens (white leghorns) were divided into three groups each consisting of 200 hens, and multhiomycin was added in an amount of 2 ppm and 10 ppm, respectively, to the feeds to be given to the respective groups except for the control group to which ordinary commercial feed for laying-hens was given, and the test was carried out by giving such feed to the respective groups continuously for six months. The test results are shown in Table 6 below. As apparent from the table, an eminent improvement in egg-laying was seen in the groups to which multhiomycin-blended feed was given.

TABLE 6

Change of average egg-laying rate (%)

| Group | 1st month from start of test | 2nd month | 3rd month | 4th month | 5th month | 6th month |
|---|---|---|---|---|---|---|
| Control | 74.2 | 80.5 | 81.2 | 82.1 | 82.0 | 82.5 |
| 2 ppm | 75.0 | 82.3 | 83.5 | 84.5 | 85.0 | 86.4 |
| 10 ppm | 74.8 | 82.9 | 85.4 | 85.6 | 85.7 | 87.1 |

EXAMPLE 9

40 weaned piglets (21 days old) were divided into four groups and commercially available piglet feed to which 0, 5, 10 and 20 ppm of multhiomycin was respectively added, was given to the respective groups continuously for four weeks, and the effects on body weight and feed efficiency were examined. As noted from Table 7 which shows the test results, the piglets bred with multhiomycin-added feed had 12.3 to 15.7% greater body weight than the piglets of the control group, and the feed efficiency was also improved by an amount of 0.32 to 0.37 over the control.

TABLE 7

Change of average body weight and feed efficiency

| Group | At start of test | 1 week later | 2 weeks later | 3 weeks later | 4 weeks later | Feed efficiency |
|---|---|---|---|---|---|---|
| Control | 4.43 | 6.44 | 8.55 | 11.21 | 13.45 | 2.02 |
| 5 ppm | 4.21 | 6.90 | 9.20 | 12.00 | 15.10 | 1.70 |
| 10 ppm | 4.50 | 6.52 | 9.44 | 12.44 | 15.35 | 1.68 |
| 20 ppm | 4.35 | 6.75 | 9.44 | 12.31 | 15.56 | 1.65 |

(Note)
Each numerical value in the table is a means value (kg).

EXAMPLE 10

80(10-week-old)of first cross pigs (Landrace X Hampshire) were divided into four groups each consisting of 20 pigs (with same number of males and females) and multhiomhcin was added in an amount of 5, 50 and 100 ppm, respectively, to the feeds shown, below and the said feed were given to the respective groups except for the control group, and such feeds were given to the pigs of the respective groups continuously for 10 weeks. To the control group, an ordinary feed was given. The results are shown in Table 8 below. It was confirmed that, at the end of the test, the average body weight of the pigs given the multhiomycin-blended feeds was higher by 11.4 to 16.1% than that of the pigs of the control group, while the feed efficiency was also improved by the 0.25 to 0.45 over the control.

TABLE 8

Change of average body weight and feed efficiency

| Group | At start of test | 2 weeks later | 4 weeks later | 6 weeks later | 8 weeks later | 10 weeks later | Feed efficiency |
|---|---|---|---|---|---|---|---|
| Control | 21.3 | 26.0 | 35.2 | 43.2 | 50.3 | 60.4 | 3.66 |
| 5 ppm | 20.1 | 27.0 | 37.5 | 45.5 | 54.5 | 67.3 | 3.41 |
| 50 ppm | 20.9 | 27.5 | 38.0 | 47.8 | 56.2 | 69.4 | 3.38 |
| 100 ppm | 21.0 | 26.9 | 37.9 | 45.9 | 57.8 | 70.1 | 3.21 |

(Note)
Each numerical value in the table is a mean value (kg).

Composition of basal feed

| Composition of basal feed | |
|---|---|
| Corn | 48.9% |
| Soybean meal | 13.0 |
| Milo | 10.0 |
| Defatted rice bran | 5.0 |
| Barley | 8.0 |
| Fish meal | 8.0 |
| Lucerne meal | 4.0 |
| Calcium carbonate | 1.4 |
| Calcium phosphate | 0.7 |
| Sodium chloride | 0.5 |
| Premix (*) | 0.5 |

(*) Premix was the same as that used in Example 6.
Note:
Malthiomycin was added to the feeds in Example 6, 8, 9 and 10 by spraying multhiomycin solution in acetone to the feed and removing acetone therefrom.

What we claim:

1. The method for preparing multhiomycin which comprises cultivating a multhiomycin producing strain belonging to the genus Streptomyces in a sulfur-containing carboxylic acid-containing liquid culture medium, said acid being selected from the group consisting of cystine and methionine which is present in an amount of 0.01–5 weight percent and isolating said multhiomycin.

2. The method according to claim 1 wherein the acid is cystine present in an amount of 0.1–3.0 weight percent.

3. The method according to claim 1 wherein the acid is methionine present in an amount of 0.05–3.0% by weight.

4. The method according to claim 1 wherein the acid is methionine present in an amount of 0.1–3.0% by weight.

5. A method for preparing multhiomycin according to claim 1 wherein the multhiomycin producing strain is Streptomyces sp. 8446-CC1 (FERM-P No. 3284).